US008707966B2

(12) United States Patent
Parrish et al.

(10) Patent No.: US 8,707,966 B2
(45) Date of Patent: Apr. 29, 2014

(54) DISINTEGRATABLE PLUG WRAPS AND THEIR APPLICATIONS

(75) Inventors: Milton E. Parrish, Midlothian, VA (US); Lixin L. Xue, Midlothian, VA (US); Jon A. Regrut, Richmond, VA (US); Marvyn Steele, Richmond, VA (US); Thomas J. Gannon, Powhatan, VA (US); Wesley Gilliam Sanderson, Chester, VA (US)

(73) Assignee: Philip Morris USA Inc., Richmond, VA (US)

( * ) Notice: Subject to any disclaimer, the term of this patent is extended or adjusted under 35 U.S.C. 154(b) by 0 days.

(21) Appl. No.: 13/532,504

(22) Filed: Jun. 25, 2012

(65) Prior Publication Data

US 2012/0325230 A1    Dec. 27, 2012

Related U.S. Application Data

(63) Continuation of application No. 13/291,828, filed on Nov. 8, 2011, now abandoned, which is a continuation of application No. 13/071,819, filed on Mar. 25, 2011, now abandoned.

(60) Provisional application No. 61/318,267, filed on Mar. 26, 2010.

(51) Int. Cl.
*A24B 15/28* (2006.01)

(52) U.S. Cl.
USPC .......................... 131/332; 131/331

(58) Field of Classification Search
USPC .......................... 131/365, 332, 331
See application file for complete search history.

(56) References Cited

U.S. PATENT DOCUMENTS

| | | | |
|---|---|---|---|
| 4,048,410 A | 9/1977 | Taylor et al. |
| 4,404,454 A | 9/1983 | Taylor et al. |
| 4,966,171 A | 10/1990 | Serrano et al. |
| 5,220,930 A | 6/1993 | Gentry |
| 5,246,017 A | 9/1993 | Saintsing et al. |
| 5,341,824 A | 8/1994 | Fletcher et al. |
| 5,462,801 A | 10/1995 | Willmund |
| 5,478,386 A | 12/1995 | Itoh et al. |
| 5,498,224 A | 3/1996 | Kauffman et al. |
| 5,574,076 A | 11/1996 | Sharak et al. |
| 5,666,976 A | 9/1997 | Adams et al. |
| 5,692,525 A | 12/1997 | Counts et al. |
| 5,692,526 A | 12/1997 | Adams et al. |
| 5,709,227 A | 1/1998 | Arzonico et al. |
| 5,804,296 A | 9/1998 | Itoh et al. |
| 5,944,278 A | 8/1999 | Stevens, III et al. |
| 5,947,126 A | 9/1999 | Wilson et al. |
| 5,988,176 A | 11/1999 | Baggett, Jr. et al. |
| 6,026,820 A | 2/2000 | Baggett, Jr. et al. |
| 6,146,497 A | 11/2000 | Nguyen |
| 6,179,804 B1 | 1/2001 | Satterfield |
| 6,550,483 B1 | 4/2003 | Dittrich |
| 6,997,190 B2 | 2/2006 | Stokes et al. |
| 7,094,193 B2 | 8/2006 | Belcastro et al. |
| 7,393,313 B2 | 7/2008 | Belcastro et al. |
| 7,789,089 B2 | 9/2010 | Dube et al. |
| 7,896,011 B2 | 3/2011 | Grubbs et al. |

OTHER PUBLICATIONS

Partial International Search Report mailed Oct. 13, 2011 for PCT/IB2011/001187.
International Search Report and Written Opinion mailed Aug. 3, 2012 for PCT/IB2011/001187.
International Preliminary Report on Patentability mailed Oct. 11, 2012 for PCT/IB2011/001187.

*Primary Examiner* — Richard Crispino
*Assistant Examiner* — Dionne Walls Mayes
(74) *Attorney, Agent, or Firm* — Buchanan Ingersoll & Rooney, PC

(57) ABSTRACT

A filter rod used in manufacture of a smoking article contains: (a) a rod of filter material, and (b) a plug wrap surrounding the rod of filter material. The overlapping side edges of the plug wrap are secured together with a plug wrap adhesive and the plug wrap adhesive comprises a disintegration accelerating agent. Alternatively or in addition, the plug wrap may contain perforations.

21 Claims, 3 Drawing Sheets

Figure 1. A plug wrap having perforations
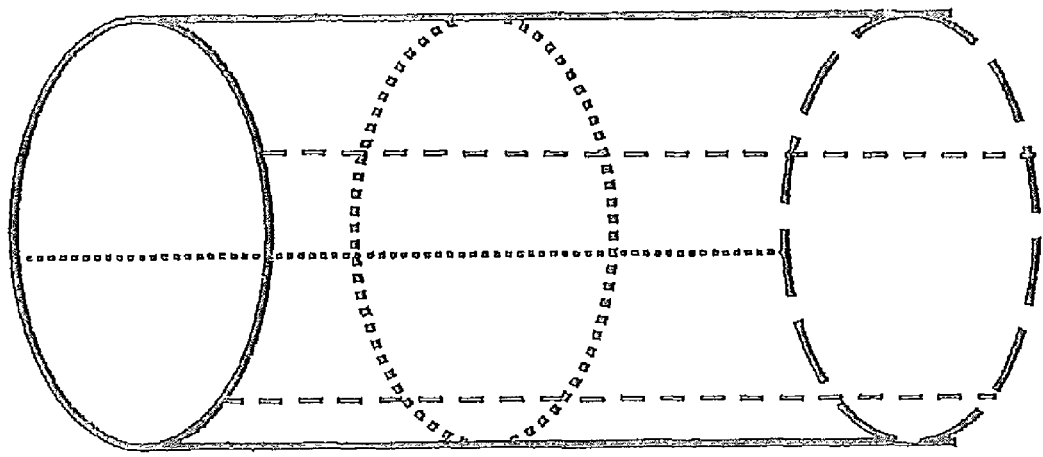

Figure 2. A plug wrap having 60 holes/inch
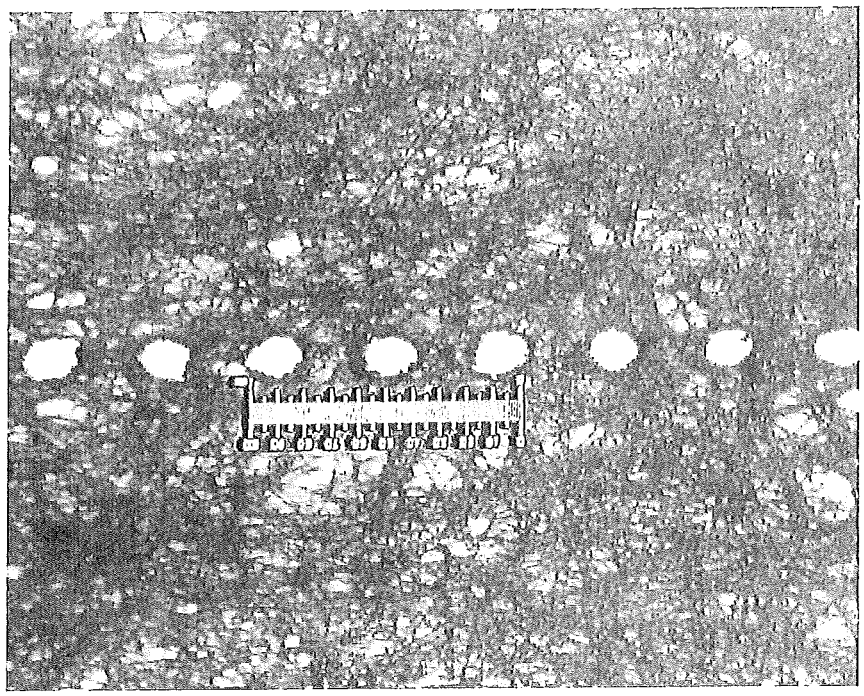

Figure 3. A plug wrap having 90 holes/inch
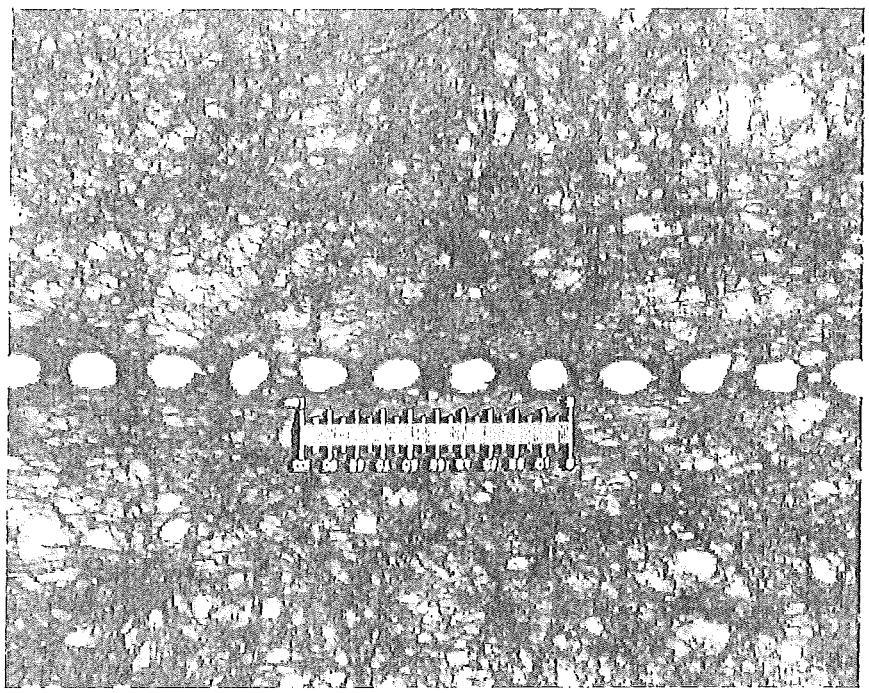

DISINTEGRATABLE PLUG WRAPS AND THEIR APPLICATIONS

CROSS REFERENCE TO RELATED APPLICATION

This application is a continuation application of U.S. application Ser. No. 13/291,828, filed on Nov. 8, 2011 now abandoned, which is a continuation application of U.S. application Ser. No. 13/071,819 entitled DISINTEGRATABLE PLUG WRAPS AND THEIR APPLICATIONS, filed on Mar. 25, 2011 now abandoned which claims priority under 35 USC §119(e) to U.S. provisional Application No. 61/318,267, filed Mar. 26, 2010, the entire content of each is incorporated herein by reference.

BACKGROUND

Smoking articles, such as cigarettes, generally have a substantially cylindrical rod shaped structure which typically includes a roll or column of smokable material, such as shredded tobacco, surrounded by a paper wrapper. Many types of cigarettes may have a cylindrical filter segment aligned in an end-to-end relationship with the tobacco rod ("filtered smoking articles"). The filter segment may comprise one or more plugs formed from a tow of filtering materials, such as cellulose acetate, circumscribed by a paper material known as "plug wrap" thereby forming a "filter plug." The opposite ends of the plug wrap can be secured together with a plug wrap adhesive. Typically, the filter segment can be attached to one end of the tobacco rod using a circumscribing wrapping material known as "tipping paper." The tipping paper and plug wrap may be bonded to each other through an "anchoring adhesive".

After a filtered smoking article is consumed, it is discarded. Adhesion of the filter plug wrap to the filter rod in the smoking article, in particular, when a non-water soluble adhesive is used, may delay the exposure of the filtering material to the environment and slow the filter disintegration, thereby contributing litter to the environment. To reduce the environmental burden of discarded filtered smoking articles, there is interest in developing cigarette filter plugs having an improved degradation rate.

SUMMARY

The present disclosure provides a filter rod used in manufacture of a smoking article, comprising (a) a rod of filter material, and (b) a plug wrap surrounding the rod of filter material with overlapping side edges of the plug wrap being secured together with a plug wrap adhesive, wherein the plug wrap adhesive comprises a disintegration accelerating agent and/or the plug wrap may contain perforations.

BRIEF DESCRIPTION OF THE DRAWINGS

FIG. 1 is a schematic illustration of an exemplary plug wrap having perforations.

FIG. 2 shows a photograph of a partial plug wrap having one row of perforations with 60 holes/inch taken by a Zeiss Stereo Light microscope.

FIG. 3 shows a photograph of a partial plug wrap having one row of perforations with 90 holes/inch taken by a Zeiss Stereo Light microscope.

DETAILED DESCRIPTION

As used herein, the term "disintegration accelerating agent" denotes an agent capable of improving disintegration rate (or accelerating disintegration) of a material, e.g., a paper, at predetermined conditions. For example, a disintegration accelerating agent can be incorporated in a plug wrap adhesive, which acts as a carrier for the disintegration accelerating agent, and upon activation, the disintegration accelerating agent can accelerate disintegration of the plug wrap, thereby helping exposure of the filtering materials to the environment for further disintegration.

As used herein, the term "smoking article" denotes an article containing a charge of smoking composition formed into a rod or column, and which may optionally be surrounded by a wrapper, which helps to hold the shape of the rod and contain the smoking composition within the smoking article. The rod of smoking material, or the wrapper therefor, or both can be burned or heated during use of the smoking article under smoking conditions. A smoking article may also contain one or more filter plugs, which can function to remove targeted constituents from, and provide aesthetically pleasing qualities to, the smoke. The term "smoking article" is intended to include cigarettes, cigars, etc. Cigarettes include both traditional cigarettes and non-traditional cigarettes.

As used herein, the term "traditional cigarette" denotes a cigarette that can be smoked by lighting an end of a wrapped rod or column of a smoking composition and drawing air predominantly through the lit end by suction at a mouthpiece end of the cigarette.

In addition, non-traditional cigarettes include, but are not limited to, cigarettes for electrical smoking systems as described in commonly-assigned U.S. Pat. Nos. 6,026,820; 5,988,176; 5,915,387; 5,692,526; 5,692,525; 5,666,976; and 5,499,636. Other non-traditional cigarettes include those having a fuel element in the tobacco rod as described in U.S. Pat. No. 4,966,171. Other non-traditional cigarettes include those having a fuel element in the tobacco rod as described in U.S. Pat. No. 4,966,171.

As used herein, the term "porous" denotes a condition which allows a liquid, a vapor or a gas to pass through it. In contrast, the term "non-porous" denotes a condition which does not allow a liquid, a vapor or a gas to pass through it.

In accordance with one embodiment, a filter plug for smoking article, comprises a filter rod and a plug wrap surrounding the filter rod, the overlapping side edges of the plug wrap being secured together with a plug wrap adhesive containing a disintegration accelerating agent.

Adhesives for the plug wrap adhesive described herein are not particularly limited and can comprise hot melt adhesives or other plug wrap adhesives. For example, the plug wrap adhesive may comprise a water insoluble hot melt adhesive. Examples of suitable water insoluble hot melt adhesives may include, but are not limited to, polyvinyl acetate and the like. Water soluble adhesives can also be used for the plug wrap adhesive described herein. Examples of suitable water soluble adhesives may include, but are not limited to, polyvinyl alcohol, and the like. When a water soluble adhesive is used as the plug wrap adhesive, it may become diluted or dissolved by moisture in the environment, and thus weaken its bonding capability. As a result, opening of the plug wrap can be accelerated. However, when a water-soluble adhesive is employed, it may be necessary to reduce the amount of water therein during manufacturing in order to effect bonding, which may lengthen and complicate the manufacturing process. In a preferred embodiment, the plug wrap adhesive is a water insoluble hot melt adhesive.

As described herein, the plug wrap adhesive can act as a carrier for the disintegration accelerating agent and release the same in an activated form when it comes into contact with sufficient moisture. For instance, water molecules can rehydrate and activate the disintegration accelerating agent, such as an enzyme, allowing the enzyme to digest the plug wrap. The weakened plug wrap paper ruptures more readily than an undigested paper. Moreover, the presence of moisture can facilitate movement of the disintegration accelerating agent from the adhesive into contact with the plug wrap.

The disintegration accelerating agent described herein preferably contains an enzyme, such as a cellulase and the like. The cellulase may be from a variety of organisms. Examples of suitable enzymes may include, but are not limited to, cellulases from *Trichoderma viride, Aspergillus niger, Sporotrichum thermophile, Chaetomium cochliodes*, etc.

The amount of the disintegration accelerating agent incorporated depends on various factors, such as the nature (e.g., activity) of the disintegration accelerating agent and the degree of disintegration desired in a specific time period. In one embodiment, an enzyme can be used in an amount of up to about 100 milligrams, and ranges therebetween including from about 1 mg to about 10 mg, from about 10 mg to about 20 mg, from about 20 mg to about 30 mg, from about 30 mg to about 40 mg, from about 40 mg to about 50 mg, from about 50 mg to about 60 mg, from about 60 mg to about 70 mg, from about 70 mg to about 80 mg, and from about 80 mg to about 90 mg, per gram of plug wrap paper. As used herein, the term "about" is intended to mean plus or minus 10% of the quantitative value described.

Optionally, the plug wrap adhesive described herein may contain stabilizers and/or antioxidants which do not interfere with the disintegration accelerating agent. Examples of suitable stabilizers and/or antioxidants may include, but are not limited to, high molecular weight hindered phenols and multifunctional phenols. Examples of suitable hindered phenols may include, but are not limited to, 1,3,5-trimethyl-2,4,6-tris (3,5-di-tert-butyl-4-hydroxy-benzyl)benzene, pentaerythritol tetrakis-3(3,5-di-tert-butyl-4-hydroxyphenyl)-propionate, n-octadecyl-3,5-di-tert-butyl-4-hydroxyphenol)-propionate, 4,4'-methylenebis(2,6-tert-butylphenol), 4,4'-thiobis(6-tert-butyl-o-cresol), 2,6-di-tert-butylphenol, 6-(4-hydroxyphenoxy)-2,4-bis(n-octyl-thio)-1,3,5-triazine, di-n-octadecyl-3,5-di-tert-butyl-4-hydroxy-benzyl-phosphonate, 2-(n-octylthio)ethyl-3,5-di-tert-butyl-4-hydroxybenzoate, and sorbitol hexa[3-(3,5-di-tert-butyl-4-hydroxyphenyl)-propionate]. Examples of suitable multifunctional phenols may include, but are not limited to, phenols containing sulfur and/or phosphorous atoms.

Furthermore, other additives may also be incorporated into the hot melt adhesive described herein in order to modify certain properties thereof. For example, colorants, such as titanium dioxide, and fillers, such as talc and clay, etc., may be incorporated in small amounts, e.g., less than about 20% by weight. Other thermoplastic and/or hydrophilic polymers may also be added to impart flexibility, toughness, strength and/or water sensitivity. Examples of suitable thermoplastic polymers may include, but are not limited to, ethylene vinyl acetate, ethylene acrylic acid, ethylene methyl acrylate and ethylene n-butyl acrylate copolymers and the like. Examples of suitable hydrophilic polymers may include, but are not limited to, polyvinyl alcohol, hydroxyethyl cellulose, hydroxypropyl cellulose, polyvinyl methyl ether, polyethylene oxide), polyvinyl pyrrolidone and the like.

The plug wrap adhesive described herein may be formulated using techniques known in the art. In an exemplary procedure, a disintegration accelerating agent is admixed with an adhesive and any other additives in a mixing vessel, preferably a heavy duty mixer which is equipped with rotors, to thereby obtain a smooth and homogeneous mass. Heat may be applied during mixing, if required or desired.

The filter rod can be made from a material which can serve as an additive carrier. The filter material may be porous or non-porous. Examples of suitable porous materials include, but are not limited to, a nonwoven material, a porous foam, poly(β-hydroxy butyrate co β'-hydroxy valerate) (PHBV), cellulose acetate (CA) fibers and mixtures thereof. Examples of suitable non-porous materials include, but are not limited to, a water-swellable polymer, a hydrophilic polymer and mixtures thereof. Examples of suitable water-swellable polymers include, but are not limited to, hydroxypropyl methylcellulose, low substituted hydroxypropyl cellulose, hydroxypropyl cellulose and mixtures thereof. Further, examples of suitable hydrophilic polymers include, but are not limited to, esters of polyvinyl alcohols, polysaccharides, alginates, pectins, gelatins, modified cellulosics, starches, super-absorbent polymers and mixtures thereof.

Preferably, the filter rod comprises a porous material. More preferably, the filter rod comprises cellulose acetate fibers.

The plug wrap which can be used in the filter plug as described herein is not particularly limited as long as it can provide the desired integrity of the filter plug. Preferably, the plug wrap is made of a moisture disintegrative sheet material, such as a paper with no wet strength chemicals. In one embodiment, the filter plug contains a cellulose-based paper.

The filter plug described herein can be manufactured by any suitable method. In one embodiment, the plug wrap adhesive can be applied to one side edge of a plug wrap paper strip and the adhesive treated plug wrap paper is wrapped circumferentially around a compressed rod of filtering material to overwrap, and thereby adhere to, the other side edge of the plug wrap paper. When heat is required, it can be applied by any convenient method, e.g., using a heated nozzle, or by direct application via a narrow wheel or roller. The applied temperature will depend, at least partially, on the adhesive material used.

According to another embodiment, a filter plug for smoking article, comprises a filter rod and a plug wrap surrounding the filter rod, the overlapping side edges of the plug wrap being secured together with a plug wrap adhesive, wherein the plug wrap contains perforations. Additionally, the plug wrap adhesive may contain a disintegration accelerating agent.

Perforations on the plug wrap can further facilitate the disintegration of the plug wrap upon disposal in the environment. Such perforations can be in any pattern, such as circular, triangular, linear, etc. In an embodiment, the perforations contain continuous cuts or lines, which may typically be vertical or longitudinal.

FIG. 1 illustrates an exemplary plug wrap having perforations. In this example, the plug wrap contains one transverse dotted line perpendicular to the length direction of the plug wrap and three axial dotted lines along the length direction of the plug wrap.

The density and size of the perforations in the plug wrap can be manipulated to retain adequate mechanical strength for the integrity of the filter plug and also serve as weak lines for the plug to open up quickly, thereby causing the exposure of internal filtering material to the environment. In an embodiment, the plug wrap contains one or more rows of perforations with about 30 to about 120 holes per linear inch. When there are one or more rows of perforations with less than about 30 holes per linear inch in the plug wrap, the accelerated disintegration effects are minimal. On the other hand, when the plug wrap contains one or more rows of perforations with more than about 120 holes per linear inch, the plug wrap may not have sufficient strength and fall apart easily, which may complicate the manufacturing process.

Preferably, the plug wrap contains one or more rows of perforations with about 60 to about 90 holes per linear inch. Each hole may have the same or different shapes and/or sizes.

Preferably, all the holes have substantially the same shape and size to simplify the manufacturing process. In one embodiment, the perforations contain substantially equally spaced ellipses. The ellipses preferably have an average major axis, along the direction of the perforations, ranging from about 0.13 mm to about 0.23 mm, and preferably, from about 0.16 mm to about 0.20 mm, and an average minor axis, perpendicular to the direction of the perforations, ranging from about 0.10 mm to about 0.20 mm, and preferably, from about 0.13 mm to about 0.17 mm.

FIG. 2 shows a photograph of a partial plug wrap having one row of perforations with 60 holes/inch where the substantially equally spaced ellipses have an average major axis of 0.19 mm±0.02 mm and an average minor axis of 0.16 mm±0.02 mm. FIG. 3 shows a photograph of a partial plug wrap having one row of perforations with 90 holes/inch where the substantially equally spaced ellipses have an average major axis of 0.18 mm±0.02 mm and an average minor axis of 0.14 mm±0.02 mm.

The perforations in the plug wrap may be created prior to, during or subsequent to the formation of the filter plug, mechanically or by thermal energy transfer (e.g. focused laser beams), printing, embossing, slitting, or other comparable functions. See, e.g., U.S. Pat. Nos. 4,404,454; 5,341,824; 5,944,278 and 7,393,313.

The plug wrap disclosed herein can be incorporated in a smoking article comprising a tobacco rod and a filter segment attached to one end of the tobacco rod, wherein the filter segment comprises a segment of the filter rod described herein. In one embodiment, the smoking article is a cigarette.

The tobaccos used in these traditional or non-traditional cigarettes are not particularly limited. Examples of suitable types of tobacco materials include, but are not limited to, cured or uncured tobacco such as flue-cured tobacco, Burley tobacco, Maryland tobacco, Oriental tobacco, rare tobacco, specialty tobacco, reconstituted tobacco, agglomerated tobacco fines, blends thereof, and the like. These materials may be used individually or in combination thereof. Alternatively or additionally, a non-tobacco smoking material may be used.

Further, the tobacco material may be provided in any suitable form. Examples of suitable forms include shreds and/or particles of tobacco lamina, processed tobacco materials, such as volume expanded or puffed tobacco, or ground tobacco, processed tobacco stems, such as cut-rolled or cut-puffed stems, reconstituted tobacco materials, blends thereof, and the like. Genetically modified tobacco may also be used.

The smoking article described herein may further contain a tipping paper circumscribing the filter segment and the tobacco rod. Preferably, the tipping paper and the plug wrap are bonded with an anchoring adhesive comprising the disintegration accelerating agent as described herein, which can facilitate detachment of the tipping paper from the plug wrap in a waste smoking article, thereby further accelerating disintegration thereof. The disintegration accelerating agent for the anchoring adhesive may be the same or different from that for the plug wrap.

The filter plug described herein can enhance disintegration of the plug wrap and thus accelerate disintegration of the filter plug. Therefore, upon disposal, disintegration of a smoking article containing such filter plug can be accelerated, thereby reducing litter to the environment.

While the invention has been described with reference to specific embodiments, variations and modifications may be made without departing from the spirit and the scope of the invention. Such variations and modifications are to be considered within the purview and scope of the invention as defined by the appended claims.

All of the above-mentioned references are herein incorporated by reference in their entirety to the same extent as if each individual reference was specifically and individually indicated to be incorporated herein by reference in its entirety.

We claim:

1. A filter rod used in manufacture of a smoking article, comprising:
    (a) a rod of filter material, and
    (b) a plug wrap surrounding the rod of filter material with overlapping side edges of the plug wrap being secured together with a plug wrap adhesive,
    wherein the plug wrap adhesive comprises a disintegration accelerating agent which comprises an enzyme, and, a water soluble or insoluble adhesive selected from the group consisting of polyvinyl acetate and polyvinyl alcohol.

2. The filter rod of claim 1, wherein the enzyme is present in an amount ranging from about 1 mg to about 100 mg per gram of the plug wrap.

3. The filter rod of claim 1, wherein the enzyme comprises a cellulase.

4. The filter rod of claim 3, wherein the cellulase comprises at least one cellulase from *Trichoderma viride, Aspergillus niger, Sporotrichum thermophile*, or *Chaetomium cochliodes*.

5. The filter rod of claim 1, wherein the plug wrap adhesive comprises a water soluble adhesive.

6. The filter rod of claim 1, wherein the plug wrap adhesive comprises a water insoluble adhesive.

7. The filter rod of claim 1, wherein the filter material is porous or non-porous.

8. The filter rod of claim 1, wherein the filter material comprises a nonwoven material, a porous foam, poly(β-hydroxy butyrate co β'-hydroxy valerate), cellulose acetate fibers or a mixture thereof.

9. The filter rod of claim 8, wherein the filter material comprises cellulose acetate fibers.

10. The filter rod of claim 1, wherein the disintegration accelerating agent is capable of improving a disintegration rate of the plug wrap.

11. A smoking article comprising:
    (a) a tobacco rod, and
    (b) a filter segment attached to one end of the tobacco rod, wherein the filter segment comprises a segment of the filter rod of claim 1.

12. The smoking article of claim 11, wherein the smoking article is a cigarette.

13. The smoking article of claim 11, further comprising:
    (c) a tipping paper circumscribing the filter segment and the tobacco rod.

14. The smoking article of claim 13, wherein the tipping paper and the plug wrap are bonded with an anchoring adhesive comprising said disintegration accelerating agent.

15. A filter rod used in manufacture of a smoking article, comprising:
    (a) a rod of filter material, and
    (b) a plug wrap surrounding the rod of filter material with overlapping side edges of the plug wrap being secured together with a plug wrap adhesive,
    wherein the plug wrap comprises one or more rows of perforations, and
    wherein the plug wrap adhesive substantially consists of a disintegration accelerating agent which comprises an enzyme, and, a water soluble or insoluble adhesive selected from the group consisting of polyvinyl acetate and polyvinyl alcohol.

16. The filter rod of claim 15, wherein the plug wrap comprises one or more rows of perforations with about 30 to about 120 holes per inch.

17. The filter rod of claim 15, wherein the plug wrap comprises one or more rows of perforations with about 60 to about 90 holes per inch.

18. A smoking article comprising:
(a) a tobacco rod, and
(b) a filter segment attached to one end of the tobacco rod, wherein the filter segment comprises a segment of the filter rod of claim 15.

19. The smoking article of claim 18, wherein the smoking article is a cigarette.

20. The smoking article of claim 18, further comprising:
(c) a tipping paper circumscribing the filter segment and the tobacco rod.

21. The smoking article of claim 20, wherein the tipping paper and the plug wrap are bonded with an anchoring adhesive comprising said disintegration accelerating agent.

\* \* \* \* \*